United States Patent
Assmus et al.

[11] Patent Number: 5,993,849
[45] Date of Patent: Nov. 30, 1999

[54] HYDROPHILIC ADHESIVE AND BINDER FOR MEDICATIONS

[75] Inventors: Manfred Assmus, Bickenbach; Thomas Beckert, Darmstadt; Guenter Bergmann, Hanau; Stephanie Kaehler, Bensheim; Hans-Ulrich Petereit, Darmstadt, all of Germany

[73] Assignee: Roehm GmbH Chemische Fabrik, Darmstadt, Germany

[21] Appl. No.: 08/995,974

[22] Filed: Dec. 22, 1997

[30] Foreign Application Priority Data

Dec. 20, 1996 [DE] Germany .................. 196 53 606

[51] Int. Cl.[6] .................................................. A61M 37/00
[52] U.S. Cl. ........................ 424/449; 424/448; 604/304
[58] Field of Search .................... 424/486, 449, 424/448; 604/890.1, 304

[56] References Cited

U.S. PATENT DOCUMENTS

| | | |
|---|---|---|
| 4,758,239 | 7/1988 | Yeo et al. . |
| 4,826,677 | 5/1989 | Mueller et al. . |
| 5,133,970 | 7/1992 | Petereit et al. . |
| 5,306,503 | 4/1994 | Muller et al. . |
| 5,438,076 | 8/1995 | Friedman et al. . |
| 5,462,744 | 10/1995 | Gupte et al. . |
| 5,466,466 | 11/1995 | Muller . |
| 5,708,021 | 1/1998 | Assmus et al. . |

OTHER PUBLICATIONS

Derwent Abstracts, AN 95–400892, JP 07 277 975, Oct. 24, 1995.

*Primary Examiner*—Edward J. Webman
*Attorney, Agent, or Firm*—Oblon, Spivak, McClelland, Maier & Neustadt, P.C.

[57] ABSTRACT

The invention relates to an adhesive and binder for dermal or transdermal therapy systems, that includes (a) 85–99.9 weight % of (meth)acrylate copolymer of structural and functional monomers, where the functional monomers have tertiary or quaternary amino groups, (b) 0.1–15 weight % of an organic dicarboxylic or tricarboxylic acid, and (c) 40–70 weight %, relative to the total of (a) and (b), of a plasticizer.

12 Claims, No Drawings

HYDROPHILIC ADHESIVE AND BINDER FOR MEDICATIONS

BACKGROUND OF THE INVENTION

1. Field of the Invention

The invention relates to an adhesive and binder for dermal and transdermal therapy systems.

2. Discussion of the Background

Adhesives and binders for pharmaceutical purposes, which are based on (meth)acrylate polymers with basic groups, in combination with plasticizers and with organic acids, are basically known.

A fundamental problem in pharmaceutical adhesives and binders is water vapor permeability. If this is not sufficient, the tolerance on the skin is impaired. In addition, there is the risk that the preparations, e.g. skin adhesive bandages, will dry up too quickly, which has a detrimental effect on the controlled release of the active substance.

Another criterion is so-called cold flow. Cold flow of an adhesive is understood to be the lack of adhesion when a force acts parallel to the adhesive surface. On the human skin, an overly high cold flow means that the adhesive bandage migrates while worn, and leaves dark edges or develops wrinkles. This is particularly disadvantageous for adhesive layers which contain active substances in transdermal therapy systems, because the absorption of the active substance by the body is influenced in an uncontrollable manner.

EP-B 415 055 relates to water-soluble pressure-sensitive skin adhesives. These consist of the salt of a non-cross-linked copolymer of a monoethylene-unsaturated, radically polymerizable monomer which contains amino groups and at least one alkyl ester of acrylic and/or methacrylic acid. The formulation is characterized in hat it is the salt of at least one higher organic carboxylic acid with 8–20 carbon atoms or a mixture of such a higher carboxylic acid with up to 30 mole % (the anionic equivalent) of medium carboxylic acids, and contains a monomer having amino groups, in the range of 30–80 weight % by weight of the copolymer, and is soluble in water in the salt form.

U.S. Pat. No. 3,321,451 describes skin adhesives that can be washed off, based on (meth)acrylate copolymers that contain amino groups, where the amino groups are partly present as the salt of an acid anion.

EP-A 164 669 describes a method for coating forms of medication by means of (meth)acrylate copolymers that contain monomers with tertiary amino groups, where these can be converted to the salt form by means of mineral acids or organic acids, such as acetic acid or citric acid, for example. The coatings are desirably as non-sticky as possible, in order to keep the coated forms of medication from sticking to each other.

EP-A 354 364 describes the use of copolymers that contain amino groups in an aqueous formation as adhesives. The amino groups are partly neutralized by acids such as fumaric acid or acetic acid, for example.

EP-A 315 218 describes pharmaceutical compositions for transdermal systemic administration of pharmacological substances, characterized in that the pharmacological substances are contained in a reservoir which contains a polyacrylate polymer with cationic properties. Additives such as plasticizers or surfactants can be present in amounts up to 50 weight %. The pharmaceutical compositions can be additionally provided with an adhesive layer, in order to achieve good adhesion on the skin.

EP-A 617 972 describes dermal therapeutical systems in layer form having a delayed release of active substance, which consists of mixtures of poly(meth)acrylates and which are produced from a melt. Here, one poly(meth)acrylate component contains functional groups, while another poly(meth)acrylate component does not contain, or contains only an insignificant amount of functional groups, and essentially regulates the flow behavior of the polymer adhesive layer.

SUMMARY OF THE INVENTION

One object of the invention is to provide an adhesive and binder suitable for transdermal and dermal therapy systems.

Another object of the invention is to provide an adhesive and binder for transdermal and dermal therapy systems having an improved tolerance on the skin.

Another object of the invention is to provide transdermal and dermal therapy systems having an improved controlled release of the active substance.

Another object of the invention is to provide an adhesive and binder for transdermal and dermal therapy systems having reduced cold flow.

These and other objects of the present invention have been achieved by means of an adhesive and binder for dermal or transdermal therapy systems, which includes: (a) 85–99.9 weight % of a (meth)acrylate copolymer of structural and functional monomers, where the functional monomers have tertiary or quaternary amino groups, (b) 0.1–15 weight % of an organic dicarboxylic or tricarboxylic acid, and (c) 40–70 weight %, relative to the total weight of (a) and (b), of a plasticizer.

Accordingly, one embodiment of the invention is an adhesive and binder, that includes:

(a) 85–99.9 weight % of a (meth)acrylate copolymer of structural and functional monomers, where the functional monomers have tertiary or quaternary amino groups, (b) 0.1–15 weight % of an organic dicarboxylic acid or tricarboxylic acid, and (c) 40–70 weight %, relative to the total weight of (a) and (b), of a plasticizer.

Another embodiment of the invention is an adhesive and binder, that includes the reaction products of:

(a) 85–99.9 weight % of a (meth)acrylate copolymer of structural and functional monomers, where the functional monomers have tertiary or quaternary amino groups, (b) 0.1–15 weight % of an organic dicarboxylic acid or tricarboxylic acid, and (c) 40–70 weight %, relative to the total weight of (a) and (b), of a plasticizer.

Another embodiment of the invention is a transdermal or dermal therapy system that includes the adhesive and binder described above and a pharmaceutically active substance.

Another embodiment of the invention is a method of delivering a pharmaceutically active substance, that includes applying the transdermal or dermal therapy system described above to the skin.

The invention is based on the recognition that the components (a), (b), and (c) must be present in defined ratios, in order to accomplish the stated task. It is assumed that the advantageous effects achieved are produced by a reciprocal or synergistic influence of the components on each other.

DESCRIPTION OF THE PREFERRED EMBODIMENTS

Various other objects, features and attendant advantages of the present invention will be more fully appreciated as the same becomes better understood from the following detailed description of the preferred embodiments, which are not intended to be limiting unless otherwise specified.

Component (a) includes (meth)acrylate copolymers of structural and functional monomers, where the functional monomers can have tertiary or quaternary amino or ammonium groups.

Preferred examples of the above copolymers have been known for some time under the product names EUDRAGIT®E, EUDRAGIT®RS, or EUDRAGIT®RL, among others.

Structural acrylate or methacrylate monomers have no functional radicals other than the vinyl function. Examples which can be names are $C_1$ to $C_4$ alkyl esters of acrylic or methacrylic acid. Methyl acrylate, ethyl acrylate, ethyl methacrylate, butyl acrylate, butyl methacylate, and methyl methacrylate are preferred.

Functional monomers are understood to be (meth)acrylate compounds which have other functional groups in addition to the vinyl function. Examples of the functional monomers include primary, secondary, and tertiary alkylamino groups, quaternary amino, sulfate, sulfonate, phosphate, phosphonate, carboxylate, hydroxy, and halo groups. Tertiary and quaternary amino and ammonium groups are especially preferred.

Dimethylaminoethyl methacrylate is particularly preferred as a monomer with functional tertiary amino groups. The content of functional monomers in component (a) with tertiary ammonium groups can advantageously lie between 30 and 70 weight %, preferably between 40 and 60 weight %.

2-trimethylammonium methyl methacylate chloride is particularly preferred as a monomer with functional quaternary amino groups. The content of functional monomers with quaternary ammonium groups is preferably between 2 and 15 weight %, most preferably between 5 and 10 weight %.

A (meth)acrylate copolymer corresponding to component (a), with tertiary amino groups, can be composed, for example, of 25 weight % methyl methacrylate, 25 weight % butyl methacrylate, and 50 weight % dimethylaminoethyl methacrylate (EUDRAGIT®E 100).

A (meth)acrylate copolymer corresponding to component (a), with quaternary amino groups, can be composed, for example, of 60 weight % methyl methacrylate, 30 weight % ethyl acrylate, and 10 weight % trimethylammonium methyl methacrylate (EUDRAGIT®RL 100).

Another preferred (meth)acrylate copolymer corresponding to component (a) with quaternary amino groups can be composed, for example, of 65 weight % methyl methacrylate, 30 weight % ethyl acrylate, and 5 weight % trimethylammonium methyl methacrylate (EUDRAGIT®RS 100).

The copolymer (a) are obtained in known manner, by radical, solution, bead, or emulsion polymerization. They can be in the form of an extruded granulate, ground powder, solution, or dispersion.

Component (b)

Organic dicarboxylic and tricarboxylic acids which are normally used for pharmaceuticals are particularly suitable. Examples of aliphatic saturated dicarboxylic acids that can be mentioned are oxalic acid, malonic acid, succinic acid, glutaric acid, and adipinic acid. Suitable aliphatic unsaturated dicarboxylic acids are maleic acid and fumaric acid. For hydroxy dicarboxylic acid, malic acid, tartaric acid, tartronic acid, and D-tartaric acid can be mentioned. Aspartinic acid is a suitable amino dicarboxylic acid. Mesoxalic acid and oxalacetic acid can be mentioned as aliphatic ketodicarboxylic acids. Suitable aromatic dicarboxylic acids are phthalic acid, isophthalic acid, and terephthalic acid. Citric acid should be mentioned among the hydroxycarboxylic acids. Among the state organic dicarboxylic and tricarboxylic acids mentioned, succinic acid (succinate), fumaric acid, and citric acid are particularly suitable. The acids may be present as alkali and alkali earth metal salts.

Component (b) can be adjusted in such a way that partial or almost complete neutralization of the tertiary amino groups in component (a) is achieved. Partial neutralization in the range of 2–50% is preferred.

Component (c)

Substances suitable as plasticizers generally have a molecular weight between 100 and 20,000 and contain one or more hydrophilic groups in the molecule, e.g. hydroxyl, ester, or amino groups. Examples of suitable plasticizers are citric acid alkyl esters, glycerin esters, phthalic acid alkyl esters, sebacinic acid alkyl esters, sucrose esters, sorbitol esters, dibutyl sebacate, and polyethylene glycols 4000 to 20,000. Preferred plasticizers are triethyl citrate and acetyl triethyl citrate.

The addition of plasticizer allows adjustment of physical properties to the requirements of the individual forms of medication, so that sufficient adhesive strength is achieved at room temperature or body temperature.

In addition, the plasticizers can advantageously reduce the melt viscosity of the polymers in the liquid state under the conditions indicated.

At room temperature, plasticizing effects are preferably evident.

Variations of the composition make it possible to balance out adverse effects of additives which are necessary for the form of medication, if necessary. Influences on the release behavior of embedded active substances are possible.

The proportion of component (a) is 85–99.9 weight %, preferably 87–95 weight %, and it is supplemented by component (b) to total 100 weight %.

If the proportion of the organic dicarboxylic or tricarboxylic acid (b) is less than 0.1 weight %, then the adhesive strength is generally not sufficient. If the proportion is above 15 weight %, this has the disadvantage that the processability is impaired. An amount proportion of the organic dicarboxylic or tricarboxylic acid (b) of 0.1–5 weight %, particularly 2–5 weight %, is preferred.

Component (c), a plasticizer, must be present in at least 40 weight % and at most 70 weight %, preferably 45–65 weight %, with reference to the total weight of components (a) and (b). If the amount of plasticizer is less than 40 weight %, sufficient skin adhesion is generally not achieved. If the proportion is above 70 weight %, it is generally difficult to control the release behavior of the active substance.

The adhesives and binders according to the invention can optionally contain other additives according to the desired properties of the specific formulation. The other additives may include but are not limited to neutral polymers, tackifiers, stabilizers, pigments, anti-oxidants, wetting agents, pore formation agents, moisturizers, complexing agents, and others.

Production Methods:

Production of the binder depends on the form of the polymer used: solid substances can be used directly, by mixing them with the additives in suitable mixers, kneaders, or extruders, which can be heated and, if necessary, evacuated. Extruders are single-screw or preferably double-screw extruders, in order to achieve suitable mixing and transport properties.

The processing temperature depends on the melt properties of the materials and preferably lies between 20° C. and 200° C. Limiting factors are the thermal stability of the substances used. Solid additives can be mixed with the polymer before extrusion. Liquid additives are added at about half the extrusion distance of the melt, and result in a reduction of viscosity and a lowering of temperature.

Polymer solutions or dispersions are preferably mixed with the additives, so that the latter dissolve or are suspended. From these solutions, dispersions, or suspensions, the binder is obtained by drying it to form thin film layers.

Processing:

Coating, granulation, sheathing or embedding take place by means of organic solution or aqueous dispersion of suitable processing aids.

Preferably, the use of melts is restricted to substances with defined melting points in the range of the processing temperatures. Most preferably, low melt viscosities are required for processing.

In one embodiment, the solid adhesive and binder according to the invention is mixed with the powders and mixed with a suitable solvent or solvents or melted together.

Adhesive layers that fix the system in place on the skin and are particularly well tolerated because of their hydrophilia are preferably obtained from solution or suspension or directly from the melt, by spreading the material out on flat carriers, for example films, woven or nonwoven textiles. Coating takes place discontinuously in the laboratory, by means of a doctor blade, and continuously on a technical scale and in production, by means of a roller doctor or roller application. Immediately after coating, a slightly adhesive, often siliconized cover film is added, which is removed before use.

The agglomerates or adhesive layers obtained can be processed further for use as forms of medication. Here, it is possible to work medications in even before production of the adhesive and binder. The pharmaceutically active substance may be preferably worked in by means of coating, spraying, or brushing on solutions, dispersions, or suspensions into melts or solid films on the adhesive and binder, and subsequently drying or cooling. These active substances are then fixed in place in particulate or dissolved form. An influence of the adhesive and binder on the release of active substance is possible and can be utilized for the formulation of forms of medication.

Formulation of the Forms of Medication

The adhesives and binders according to the invention can be used as a component of a transdermal therapy system. Typically, this involves an adhesive bandage that includes the adhesive and binder, which contains a pharmaceutical drug that acts locally after release, or is absorbed into the bloodstream, distributed in the body, and acts systemically there. Dermal and transdermal therapy systems often have a multi-layer structure and are differentiated in accordance with their structural design, as reservoir systems, matrix systems, drug-in-adhesive systems, or multi-laminate systems.

The drug is embedded in one or more layers of these systems, and is subject to controlled release after being fixed in place on the skin, in order to develop the desired effect.

Transdermal systems according to the invention can contain the active substances characterized in general below, which are used on or in the human in animal body, in order to 1. heal, relieve, prevent or detect diseases, illnesses, bodily injury, or pathological disorders;
2. detect the composition, the state, or the function of the body or psychological conditions;
3. replace active substances or bodily fluids produced by the human or animal body;
4. combat or eliminate disease pathogens, parasites, or substances foreign to the body, or render them harmless;
5. influence the composition, the state, or the functions of the body or psychological conditions.

Preferred drugs usually used can be found in reference works such as the Rote Liste (Red List) or the Merck Index, the entire contents of which are hereby incorporated by reference.

All the drugs which fulfill the desired therapeutic effect in the sense of the above definition and possess sufficient stability as well as penetration ability through the skin can be used according to the invention.

Important examples of groups and individual substances, without any claim to completeness, are the following:

analgesics, anti-allergics, anti-arrhythmics, antibiotics, chemotherapeutics, antidiabetics, antidotes, anti-epileptics, antihypertensives, antihypotensives, anticoagulants, antimycotics, antiphlogistics, beta receptor blockers, calcium antagonists, and ACE inhibitors, broncholytics/antiasthmatics, cholinergics, corticoids (internal), dermatics, diuretics, enzyme inhibitors, enzyme preparations, and transport proteins, expectorants, geriatrics, gout medications, flu medications, hormones and their inhibitors, hypnotics/sedatives, cardiac medications, lipid lowering agents, parathyroid hormone/calcium metabolism regulators, psychopharmaceuticals, sex hormones and their inhibitors, spasmolytics, sympathomimetics, vitamins, would treatment medications, cytostatics.

Transdermal systems according to the invention can preferably contain the following drugs: nicotine, glycerol trinitrate, scopolamine, clonidine, fentanyl, estradio, testosterone, oxybutynine, dichlophenac, ibuprofen, ketoprofen, diltiazem, propranolol, albuterol, alprazolam, amethocaine, atenolol, benzoporphyrine, buprenorphine, calcitonin, dithranol, diphencypron, diverse peptides, eptazocine, ethinyl estradiol, methotrexate, naloxone, and tretinoin and salicylic acid.

Forms of medication can be produced from the intermediate stages produced according to the invention, by means of usual processing techniques.

Carriers coated with the adhesive and binder are generally present in rolled form, protected by cover layers (release liners). From these rolls, individual adhesive bandages of the required size are cut or punched, and individually packaged.

Coating flat carriers with liquids that contain polymers are described, for example, in Mass. J., and Schmidt, H.: Coating Technology for Transdermal Drug Delivery Systems, Medical Device Technology, Edition 3/4 1990, p. 46–50, the entire contents of which are hereby incorporated by reference.

Non-woven textiles or foils/films are preferred as flat carriers.

Non-woven textiles, also called "non-wovens," consist of natural or synthetic substances. They can be coated in order to improve their processing. Foils/films generally consist of metal (aluminum) or plastics, e.g. polyolefins, polyesters, or polyacrylates. Often, coated starting materials are used. Thin metal layers, for example, prevent penetration of the embedded drug into the plastic during storage. Primers promote adhesion of the layers on one another.

Properties relevant for the application, required tests, and specifications for the forms of medicine are listed in drug compendia. Details can be found in generally available texts, the entire contents of each of which are hereby incorporated by reference, e.g.:

Voigt, R. (1984): Lehrbuch der pharmazeutischen Technologie (Manual of Pharmaceutical Technology); Verlag chemie, Weinhem - Beerfield Beach, Florida Basel.

Sucker, H., Fuchs, P., Speiser, P.: Pharmzeutische Technologie (Pharmaceutical Technology), Georg Thieme Verlag Stuttgart (1991), particularly Chapters 15 and 16, p. 626–642.

Gennaro, A. R. (editor), Remington's Pharmaceutical Sciences, Mack Publishing Co., Easton Pa. (1985), Chapter 88, p. 1567–1573.

Heilmann, K.: Therapeutische Systeme (Therapeutic Systems), Ferdinand Euler Verlag, Stuttgart, p. 52–57.

Brandau, R. and Lippold, B. H. (1982): Dermal and Transdermal Absorption, Wissenschaftliche Verlagsgesellschaft MbH, Stuttgart, p. 171–200.

EXAMPLES

Having generally described this invention, a further understanding can be obtained by reference to certain specific examples which are provided herein for purposes of illustration only and are not intended to be limiting unless otherwise specified.

Determination of the adhesive strength is performed by pulling off a strip, preferably made of aluminum, which is 50 mm wide and coated with the adhesive and binder, from a VA steel plate, while simultaneously measuring the force required to do so. The method is analogous to the European Pharmacopoeia (Peel Method).

The minimum adhesive strength required for adhesive bandages can be defined in different ways, depending on the purpose of use. According to the invention, this value is at least 10 N/50 mm.

Cold flow is measured according to defined convention methods, e.g. PSTC-7 or AFERA 4012-P1.

For purposes of human medicine, however, it is more practical to take "natural" test conditions of the human skin into consideration (degree of warmth of the skin, moisture). In addition, the influence of different skin types should be considered. For quantification of cold flow on the human skin, the following method can be used, for example.

A group of test subjects wears test adhesive bandages over a period of 24 hours, under conditions that remain the same. Then migration, i.e. slippage of the adhesive bandages is measured in mm, and the following assessment is made with regard to cold flow.

Break-down:

| very good | -5- | 0 mm slippage |
| good | -4- | 1 mm slippage |
| medium | -3- | 2–3 mm slippage |
| poor | -2- | 4–6 mm slippage |
| very poor | -1- | adhesive bandage develops wrinkles |

Example 1: Adhesive layer for dermal and transdermal therapy systems from organic solution 40 g EUDRAGIT®E 100 (copolymer of 25 weight % methyl methacrylate), 25 weight % butyl methacrylate, and 50 weight % dimethylaminoethyl methacrylate; manufactured by Röhm GmbH, D-64293 (Darmstadt, Germany) are dissolved in a mixture of 24 g acetone, 9 g ethanol, and 3 g isopropanol. 20 g acetyl triethyl citrate (ATEC), and, at high stirring speed, 1 g citric acid, as a 25% solution in ethanol, are worked into this solution. A layer of the adhesive, with a thickness of 200 µm, is dried on an aluminum foil with a thickness of 50 µm, for 10 min, at 60° C. A clear layer with a thickness of approx. 110 µm is obtained, which demonstrates an adhesive strength of 66.1 N (N/50 mm), measured by analogy to the Peel method Ph. Eur. II.

Example 2: Adhesive layer for dermal and transdermal therapy systems from organic solution 40 g EUDRAGIT®E 100 are dissolved in a mixture of 24 g acetone, 9 g ethanol, and 3 g isopropanol. 20 g tributyl citrate (TBC), and, at high stirring speed, 1 g citric acid (2.5% with reference to the polymer), as a 25% solution in ethanol, are worked into this solution. A layer of the adhesive, with a thickness of 200 µm, is dried on an aluminum foil with a thickness of 50 µm, for 10 min, at 60° C., and demonstrates an adhesive strength of 50.6 N (N/50 mm), measured by analogy to the Peel method Ph. Eur. II.

Example 3: Adhesive layer for dermal and transdermal therapy systems from organic solution 40 g EUDRAGIT®E 100 are dissolved in a mixture of 24 g acetone, 9 g ethanol, and 3 g isopropanol. 20 g tributyl citrate (ATBC), and, at high stirring speed, 1 g citric acid, as a 25% solution in ethanol, are worked into this solution. A layer of the adhesive, with a thickness of 200 µm, is dried on an aluminum foil with a thickness of 50 µm, for 10 min, at 60° C. A clear layer with a thickness of approx. 110 µm forms, which demonstrates an adhesive strength of 68.5 (N/50 mm), measured by analogy to the Peel method Ph. Eur. II.

Example 4: Adhesive layer for dermal and transdermal therapy systems from organic solution 40 g EUDRAGIT®E 100 are dissolved in a mixture of 24 g acetone, 12 g ethanol, and 3 g isopropanol. 25.3 g acetyl tributyl citrate (ATBC), and, at high stirring speed, 1.6 g succinic acid, which was previously dissolved in 24 g ethanol, are worked into this solution. This solution is applied as a coating as described in Example 3. Round adhesive bandages with a diameter of 43 mm are punched from the foil. These samples adhere firmly to the human skin and can be pulled off without leaving a residue (adhesive strength: 58 (N/50 mm)).

Example 5: Adhesive layer for dermal and transdermal therapy systems from organic solution 40 g EUDRAGIT®E 100 are dissolved in a mixture of 24 g acetone, 12 g ethanol, and 3 g isopropanol. 20.0 g acetyl triethyl citrate (ATEC), and, at high stirring speed, 1.0 g succinic acid, which was previously dissolved in 15 g ethanol, are worked into this solution. This solution is applied as a coating as described in Example 3 and dried for 10 min, at 60° C. A clear layer with a thickness of approx. 110 µm forms, which demonstrates an adhesive strength of 62.1 (N/50 mm), measured by analogy to the Peel method Ph. Eur. II. Round adhesive bandages with a diameter of 43 mm are punched from the foil. These samples adhere firmly to the human skin and can be pulled off without leaving a residue.

Example 6: Adhesive layer for dermal and transdermal therapy systems from organic solution 40 g EUDRAGIT®E 100 are dissolved in a mixture of 24 g acetone, 12 g ethanol, and 3 g isopropanol. 20.0 g acetyl triethyl citrate (ATEC), and, at high stirring speed, 1.0 g fumaric acid, which was previously dissolved in 18 g ethanol, are worked into this solution. This solution is applied as a coating as described in Example 3 and dried for 10 min, at 60° C. A clear layer with a thickness of approx. 110 μm forms, which demonstrates an adhesive strength of 76.5 (N/50 mm), measured by analogy to the Peel method Ph. Eur. II. Round adhesive bandages with a diameter of 43 mm are punched from the foil. These samples adhere firmly to the human skin and can be pulled off without leaving a residue.

Example 7: Adhesive layer for dermal and transdermal therapy systems from organic solution 40 g EUDRAGIT®E 100 are dissolved in a mixture of 24 g acetone, 12 g ethanol, and 3 g isopropanol. 16.0 g acetyl triethyl citrate (ATEC), and, at high stirring speed, 0.9 g citric acid, which was previously dissolved in 18 g ethanol, are worked into this solution. This solution is applied as a coating as described in Example 3 and dried for 10 min, at 60° C. A clear layer with a thickness of approx. 110 μm forms, which demonstrates an adhesive strength of 58.0 (N/50 mm), measured by analogy to the Peel method Ph. Eur. II. Round adhesive bandages with a diameter of 43 mm are punched from the foil. These samples adhere firmly to the human skin and can be pulled off without leaving a residue.

Example 8: Adhesive layer for dermal and transdermal therapy systems from organic solution 40 g EUDRAGIT®E 100 are dissolved in a mixture of 24 g acetone, 12 g ethanol, and 3 g isopropanol. 20.0 g acetyl triethyl citrate (ATEC), and, at high stirring speed, 1.5 g citric acid, which was previously dissolved in 18 g ethanol, are worked into this solution. This solution is applied as a coating as described in Example 3 and dried for 10 min, at 60° C. A clear layer with a thickness of approx. 110 μm forms, which demonstrates an adhesive strength of 72.6 (N/50 mm), measured by analogy to the Peel method Ph. Eur. II. Round adhesive bandages with a diameter of 43 mm are punched from the foil. These samples adhere firmly to the human skin and can be pulled off without leaving a residue.

Example 9: Adhesive layer for dermal and transdermal therapy systems from organic solution 40 g EUDRAGIT®E 100 are dissolved in a mixture of 24 g acetone, 12 g ethanol, and 3 g isopropanol. 16.0 g acetyl triethyl citrate (ATEC), and, at high stirring speed, 0.17 g citric acid, which was previously dissolved in 18 g ethanol, are worked into this solution. This solution is applied as a coating as described in Example 3 and dried for 10 min, at 60° C. A clear layer with a thickness of approx. 110 μm forms, which demonstrates an adhesive strength of 60.1 (N/50 mm), measured by analogy to the Peel method Ph. Eur. II. Round adhesive bandages with a diameter of 43 mm are punched from the foil. These samples adhere firmly to the human skin and can be pulled off without leaving a residue.

Example 10: Adhesive layer for dermal and transdermal therapy systems from organic solution 40 g EUDRAGIT®E 100 are dissolved in a mixture of 24 g acetone, 9 g ethanol, and 3 g isopropanol. 20.0 g triethyl citrate (TEC), and, at high stirring speed, 1 g citric acid (2.5% with reference to the polymer), as a 25% solution in ethanol, are worked into this solution. A layer of the adhesive, with a thickness of 200 μm, is dried on an aluminum foil with a thickness of 50 μm, for 10 min, at 60° C., and demonstrates an adhesive strength of 58.8 N (N/50 mm), measured by analogy to the Peel method Ph. Eur. II.

COMPARISON EXAMPLES

Preparations in which the amount proportions were outside of the invention (Examples C1–C18) were tested with regard to hydrophilia, adhesive strength, and cold flow. The results are shown in Table 1, in a comparison with Examples 1–10.

| Example | a weight % | b weight % | c weight % (rel. to a + b) | Hydrophilia WDD (gH20/m²xd) DIN 53 122 | Adhesive strength (N/50 mm) | Cold flow* |
|---|---|---|---|---|---|---|
| 1 | 97.5 (E) | 2.5 C | 48.7 ATEC | 480 | 66 | 5 |
| 2 | 97.5 (E) | 2,5 C | 48.7 TBC | 410 | 51 | 3 |
| 3 | 97.5 (E) | 2.5 C | 48.7 ATBC | 375 | 69 | 3 |
| 4 | 96.0 (E) | 4.0 B | 60.8 ATBC | 392 | 58 | 5 |
| 5 | 97.5 (E) | 2.5 B | 48.7 ATEC | 410 | 62 | 5 |
| 6 | 97.5 (E) | 2.5 F | 48.7 ATEC | 420 | 77 | 3 |
| 7 | 97.9 (E) | 2.1 C | 40.0 ATEC | ca 490*** | 58 | 4 |
| 8 | 96.5 (E) | 3.5 C | 50.0 ATEC | ca 400*** | 73 | 5 |
| 9 | 99.6 (E) | 0.4 C | 40,0 ATEC | 472 | 60 | 3 |
| 10 | 97.5 (E) | 2.5 C | 48.7 TEC | 510 | 59 | 4 |
| C 1 | 100 (RS) | — | 50.0 TEC | ca 300*** | 22 | —** |
| C 2 | 100 (RL) | — | 50.0 TEC | ca 500*** | <10 | —** |
| C 3 | 100 (RL) | — | 30.0 TEC | ca 470*** | <10 | —** |
| C 4 | 100 (RS) | — | 20.0 TEC | 250 | <10 | —** |
| C 5 | 100 (RL) | — | 80.0 TEC | —** | <10 | —** |
| C 6 | 100 (RS) | — | 100.0 TEC | —** | <10 | —** |
| C 7 | 97.9 (E) | 2.1 C | 80.0 ATEC | 460** | 86 | 2 |
| C 8 | 80.2 (E) | 19.8 C | 50.0 ATEC | —** | <10 | —** |

*scale from 1 = very poor to 5 = very good
**not determined, since the adhesive strength was too low
***estimated (N/50 mm), measured by analogy to the Peel method Ph. Eur. II. Round adhesive bandages with a diameter of 43 mm E=copolymer of 25 weight % methyl methacrylate, 25 weight % butyl methacrylate, and 50 weight % dimethylaminoethyl methacrylate (EUDRAGIT®E 100, Röhm GmbH, D-64293 Darmstadt, Germany)

RS=copolymer of 65 weight % methyl methacrylate, 30 weight % ethyl acrylate, and 5 weight % trimethylammonium methyl methacrylate chloride (EUDRAGIT®RS, Röhm GmbH, D-64293 Darmstadt, Germany)

L=copolymer of 60 weight % methyl methacrylate, 30 weight % ethyl acrylate, and 10 weight % 2-trimethylammonium methyl methacrylate chloride (EUDRAGIT®RL, Röhm GmbH, D-64293 Darmstadt, Germany)

ATBC=acetyl tributyl citrate; ATEC=acetyl triethyl citrate; TBC=tributyl citrate; TEC triethyl citrate C=citric acid; B=succinic acid; F=fumaric acid

Having now fully described the invention, it will be apparent to one of ordinary skill in the art that many changes and modifications can be made thereto without departing from the spirit or scope of the invention as set forth herein.

This application is based on German Patent application 196 53 606.5, filed Dec. 20, 1996, the entire contents of which are hereby incorporated by reference.

What is claimed as new and desired to be secured by Letters Patent of the United States:

1. An adhesive and binder system for dermal or transdermal therapy, comprising:
   (a) 85–99.9 weight %, based on the total weight of (a) and (b), of a (meth)acrylate copolymer of structural and functional monomers, where the functional monomers have tertiary or quaternary amino groups,
   (b) 0.1–15 weight %, based on the total weight of (a) and (b), or an organic dicarboxylic or tricarboxylic acid,
   (c) 40–70 weight %, relative to the total weight of (a) and (b) of a plasticizer of molecular weight between 100 and 20,000 containing one or more hydrophilic groups, and
   (d) a therapeutically effective amount of pharmaceutically active substance.

2. The adhesive and binder according to claim 1, wherein the proportion of dicarboxylic or tricarboxylic acid (b) is 5–0.1 weight %.

3. The adhesive and binder according to claim 1, wherein the proportion of plasticizer (c) is 45 to 65 weight %.

4. The adhesive and binder according to claim 1, wherein the proportion of dicarboxylic or tricarboxylic acid (b) is 0.1 to 5 weight %, based on the total weight of (a) and (b).

5. The adhesive and binder according to claim 1, wherein the structural monomer comprises $C_{1-4}$ alkyl esters of acrylic methacrylic acid.

6. The adhesive and binder according to claim 5, wherein the structural monomer is at least one monomer selected from the group consisting of methyl acrylate, ethyl acrylate, ethyl methacrylate, butyl acrylate, butyl methacrylate, and methyl methacrylate, and a mixture thereof.

7. The adhesive and binder according to claim 1, wherein the functional monomer comprises acrylate and methacrylate monomers having tertiary amino or quaternary ammonium group attached thereto.

8. The adhesive and binder according to claim 1, wherein the (meth)acrylate copolymer (a) comprises 30–70 weight % of the functional monomer.

9. The adhesive and binder according to claim 1, wherein the organic dicarboxylic or tricarboxylic acid comprises at least one acid selected from the group consisting of aliphatic saturated and unsaturated dicarboxylic acids, amino dicarboxylic acids, aromatic dicarboxylic acids, keto acids, and hydroxy acids, and mixtures thereof.

10. The transdermal or dermal therapy system according to claim 1, wherein the pharmaceutically active substance is selected from the group consisting of nicotine, glycerol trinitrate, scopolamine, clonidine, fentanyl, estradiol, testosterone, oxybutynine, dichlophenac, ibuprofen, ketoprofen, diltiazem, propranolol, albuterol, alprazolam, amethocaine, atenolol, benzoporphyrine, buprenorphine, calcitonin, dithranol, diphencypron, diverse peptides, eptazocine, ethinyl estradiol, methotrexate, naloxone, and tretinoin, and salicylic acid and mixtures thereof.

11. A method of administering a pharmaceutically active substance, comprising applying the transdermal or dermal therapy system according to claim 1 to the skin.

12. The system of claim 1 wherein (c) is a citric acid alkyl ester.

* * * * *